(12) United States Patent
Bovet et al.

(10) Patent No.: US 9,808,423 B2
(45) Date of Patent: Nov. 7, 2017

(54) PREPARATION OF SUSPENSION AEROSOL FORMULATIONS

(75) Inventors: Li Li Bovet, Chapel Hill, NC (US); Jay T. Holt, Raleigh, NC (US)

(73) Assignee: Generics [UK] Limited, Hertfordshire (GB)

( * ) Notice: Subject to any disclaimer, the term of this patent is extended or adjusted under 35 U.S.C. 154(b) by 2205 days.

(21) Appl. No.: 11/665,093

(22) PCT Filed: Oct. 12, 2005

(86) PCT No.: PCT/GB2005/050183
§ 371 (c)(1),
(2), (4) Date: Jun. 1, 2009

(87) PCT Pub. No.: WO2006/040598
PCT Pub. Date: Apr. 20, 2006

(65) Prior Publication Data
US 2009/0297457 A1 Dec. 3, 2009

Related U.S. Application Data

(60) Provisional application No. 60/617,686, filed on Oct. 12, 2004.

(51) Int. Cl.
| | |
|---|---|
| A61K 9/12 | (2006.01) |
| A61M 16/10 | (2006.01) |
| A61M 15/00 | (2006.01) |
| A61K 9/10 | (2006.01) |
| A61K 9/00 | (2006.01) |

(52) U.S. Cl.
CPC ............ *A61K 9/10* (2013.01); *A61K 9/008* (2013.01); *A61K 9/0043* (2013.01)

(58) Field of Classification Search
USPC .......................................................... 424/45
See application file for complete search history.

(56) References Cited

U.S. PATENT DOCUMENTS

| | | | |
|---|---|---|---|
| 3,014,844 A | 12/1961 | Thiel et al. | |
| 4,352,789 A | 10/1982 | Thiel | |
| 5,795,594 A | 8/1998 | York et al. | |
| 5,849,265 A | 12/1998 | Li-Bovet et al. | |
| 6,743,413 B1 * | 6/2004 | Schultz et al. | 424/45 |
| 2003/0032632 A1 * | 2/2003 | Crispps et al. | 514/179 |
| 2003/0114428 A1 * | 6/2003 | Sequeira et al. | 514/170 |
| 2004/0042973 A1 * | 3/2004 | Chaudhry et al. | 424/46 |

FOREIGN PATENT DOCUMENTS

| | | | | |
|---|---|---|---|---|
| GB | 2 140 800 A | | 12/1984 | |
| GB | WO00/38811 | * | 7/2000 | ............ B01D 9/00 |
| WO | WO 98/13031 A2 | | 4/1998 | |
| WO | WO 02/30394 A2 | | 4/2002 | |
| WO | WO 2004/045621 A1 | | 6/2004 | |
| WO | WO 2004/054545 A1 | | 7/2004 | |

OTHER PUBLICATIONS

Salmeterol xinafoate MSDS (www.seqchem.com/safetysheet.php?SQIndex=SPR01045s).*
Albuterol MSDS (http://dailymed.nlm.nih.gov/dailymed/archives/fdaDrugInfo.cfm?archiveid=2526).*
[No Author Listed] Aerosol spray. Wikipedia, the free encyclopedia. Last accessed at http://en.wikipedia.org/wiki/Aerosol_spray on Aug. 7, 2006.
[No Author Listed] Definition of "solution". Stedman's Medical Dictionary.
[No Author Listed] Monographs, Salbutamol Sulphate. European Pharmacopoeia 5.0. 2005. pp. 7, 2393.

* cited by examiner

*Primary Examiner* — Mina Haghighatian
*Assistant Examiner* — Erin Hirt
(74) *Attorney, Agent, or Firm* — Wolf, Greenfield & Sacks, P.C.

(57) ABSTRACT

The present invention provides processes for preparing suspension aerosol formulations, wherein the particles for inhalation are formed in situ during the process of manufacturing the formulation. In one aspect of the invention, a process for preparing a suspension aerosol formulation comprises the steps of: (a) dissolving one or more medicaments in one or more solvents to form a solution; and (b) mixing one or more propellants with the solution under conditions effective to precipitate, entirely or partially, at least one of the medicaments.

59 Claims, 7 Drawing Sheets

Fig. 3

Particle Size Distributions of Salmeterol Xinafoate Formulations

Fig. 4

Particle Size Distribution of a Formulation Prepared from a Mixture of Ethanol and Salmeterol Xinafoate, wherein the Salmeterol Xinafoate is Partially Dissolved

Fig. 5

Particle Size Distributions of a 2% EtOH / 1% Oleic Acid / HFA-134a Formulation Prepared by Dissolution in a Solvent followed by Precipitation vs. Prepared Conventionally

PREPARATION OF SUSPENSION AEROSOL FORMULATIONS

RELATED APPLICATIONS

This application is a national stage filing under 35 U.S.C. §371 of international application PCT/GB2005/050183, filed Oct. 12, 2005, which was published under PCT Article 21(2) in English.

FIELD OF THE INVENTION

The present invention relates in general to medicinal aerosol formulations and in particular to processes of preparing suspension aerosol formulations for use in inhalation therapy.

BACKGROUND OF THE INVENTION

Pressurized metered dose inhalers (MDIs) are widely used devices for the delivery of medicaments to the respiratory tract by inhalation via the oral and nasal routes. Though MDIs are used primarily for topical delivery of drugs to the respiratory tract for treatment of such diseases as asthma and chronic obstructive pulmonary disease (COPD), there is increasing interest in their use for systemic drug delivery. Classes of medicaments commonly delivered by MDIs include bronchodilators (e.g., beta-agonists and anticholinergics), corticosteroids, and anti-allergics. See Anthony Hickey, *Pharmaceutical Inhalation Aerosol Technology*, Marcel Decker, New York (2004) for a general background on this form of therapy.

MDI formulations are comprised of, at least, a medicament and a propellant. MDI formulations may further comprise one or more excipients other than propellant.

MDI formulations are generally characterized as either solutions or suspensions. A solution formulation comprises the medicament dissolved or solubilized in propellant or in a mixture of propellant and one or more excipients. A suspension formulation contains the medicament in the form of particles which are dispersed in the propellant or in a mixture of propellant and one or more other excipients.

Traditionally, the propellant system used in MDIs has consisted of one or more chlorofluorocarbons (CFCs), such as Freon 11 ($CCl_3F$), Freon 12 ($CCl_2F_2$), and Freon 114 ($CF_2ClCF_2Cl$). However, the CFC propellants are now believed to provoke the degradation of stratospheric ozone and thus their production and use are being phased out.

Hydrofluoroalkane (HFA) propellants, particularly 1,1,1,2-tetrafluoroethane (HFA-134a) and 1,1,1,2,3,3,3-heptafluoropropane (HFA-227), are currently favored as non-ozone depleting alternatives to the CFC propellants for respiratory drug delivery. Other alternatives to CFCs have been proposed, including dimethyl ether and low molecular weight hydrocarbons, such as propane and butane.

The efficiency of an aerosol device, such as an MDI, is a function of the dose deposited at the appropriate site in the respiratory tract. Deposition is affected by several factors, of which one of the most important is the aerodynamic particle size. The distribution of aerodynamic particle sizes of solid particles and/or droplets in an aerosol can be characterized by their mass median aerodynamic diameter (MMAD, the diameter around which the mass aerodynamic diameters are distributed equally) and geometric standard deviation (GSD, the measure of variability of the aerodynamic particle diameters). Aerosol particles of equivalent MMAD and GSD have similar deposition in the respiratory tract irrespective of their composition.

For inhalation therapy, there is a preference for aerosols in which particles for inhalation have an MMAD of about 0.5 to 100 µm, depending on the intended site of deposition. Particles smaller than 0.5 µm may be exhaled, and particles larger than 100 µm may clog the metering valve or actuator orifice.

For inhalation therapy targeting the lungs, there is a preference for aerosols in which the particles for inhalation have an MMAD of about 0.5 to 10 µm, more preferably about 0.5 to 5 µm, and most preferably about 0.5 to 3 µm. Particles larger than about 5 µm in diameter are primarily deposited by inertial impaction in the oropharynx, particles of about 0.5 to 5 µm in diameter are ideal for deposition in the conducting airways, and particles of about 0.5 to 3 µm in diameter are desirable for aerosol delivery to the lung periphery.

For inhalation therapy targeting the nose, where the medicament is either for the topical treatment of tissues within the nose, or to be absorbed, so as to have a systemic effect, via the nasal mucosa (i.e., via the so called intranasal route), there is a preference for aerosols in which the particles for inhalation have an MMAD of about 5 to 100 µm, preferably about 5 to 50 µm, more preferably about 5 to 25 µm, or, when penetration beyond the nasal cavity is undesirable, within the range of about 10 to 100 µm, preferably about 10 to 50 µm and more preferably about 10 to 25 µm.

Numerous methods are known in the art for the preparation of suspension aerosol formulations for MDIs. The known methods generally comprise the mixing of preformed medicament powders, which are of a size suitable for inhalation therapy, with propellant and optionally one or more other excipients. Control of the particle size distribution of the aerosol particles generated from the suspension aerosol formulation is accomplished primarily via control of the particle size distribution of the medicament powders used to prepare the formulation. Thus, considerable care is normally taken to avoid dissolution of the medicament powder in the excipients, as any dissolution of the medicament powder during manufacture of the formulation would result in loss of particle size control.

Conventional methods for generating medicament powders suitable for preparation of formulations for inhalation therapy, such as suspension aerosol formulations for MDIs, include milling (micronization), spray drying, and supercritical fluid recrystallization.

The conventional processes of MDI manufacture are generally characterized as either "pressure filling" or "cold filling". In pressure filling, the powdered medicament, optionally combined with one or more excipients, is placed in a suitable aerosol container capable of withstanding the vapor pressure of the propellant and fitted with a metering valve. The propellant is then forced as a liquid through the valve into the container. In an alternate process of pressure filling, the particulate drug is combined in a process vessel with propellant and optionally one or more excipients, and the resulting drug suspension is transferred through the metering valve fitted to a suitable MDI container. In cold filling, the powdered medicament, propellant which is chilled below its boiling point, and optionally one or more excipients are added to the MDI container, and a metering valve is fitted to the container. For both pressure filling and cold filling processes, additional steps, such as mixing, sonication, and homogenization, are often advantageously included. See Lachman et al. in *The Theory and Practice of Industrial Pharmacy*, Lea & Febiger, Philadelphia (1986) for an overview of conventional manufacturing procedures for MDIs.

Salmeterol xinafoate is a selective and potent beta adrenoreceptor stimulant bronchodilator which has been very successfully used by inhalation for the immediate relief of spasm in asthma. Salmeterol is described in British Patent Specification No 2140800. The xinafoate salt of salmeterol is a particularly preferred pharmaceutically acceptable salt for use in inhalation therapy.

Fenoterol is an adrenergic bronchodilator used for the treatment of asthma and COPD. The hydrobromide salt of fenoterol is a particularly preferred pharmaceutically acceptable salt for use in inhalation therapy.

Ipratropium is an anticholinergic bronchodilator used by inhalation for the treatment of asthma, COPD, and allergic rhinitis. The bromide salt of ipratropium is a particularly preferred pharmaceutically acceptable salt for use in inhalation therapy.

BRIEF SUMMARY OF THE INVENTION

The present invention provides processes for preparing suspension aerosol formulations suitable for inhalation therapy, wherein the medicament particles for inhalation are formed in situ during the process of manufacturing the formulation.

Accordingly, the present invention provides, in a first aspect, a method of preparing a suspension aerosol formulation comprising a particulate medicament and a propellant, wherein a medicament solution is mixed with the propellant under conditions that cause a precipitate of the medicament to be formed from the solution.

The precipitate preferably comprises particles of the medicament in a form suitable for use in inhalation therapy. The precipitate can comprise particles of the medicament in a form suitable for administration to the lungs via oral or nasal inhalation, or for administration to the internal tissues of the nose via nasal inhalation. The propellant is preferably a liquefied propellant gas.

In another aspect of the invention, a process for preparing a suspension aerosol formulation comprises the steps of:
 (a) dissolving one or more medicaments in one or more solvents to form a solution; and
 (b) mixing one or more propellants with the solution under conditions effective to precipitate, entirely or partially, at least one of the medicaments.

The mixing of the propellant with the solution may be accomplished by adding the propellant to the solution or by adding the solution to the propellant.

The precipitation of the medicament may be performed within an aerosol container. Alternatively, the suspension aerosol formulation may be transferred to the aerosol container after precipitation of the medicament.

The processes of the invention may be controlled to achieve desired characteristics of the medicament particles generated in the suspension aerosol formulation. Such characteristics include, but are not limited to, particle size and size distribution, particle shape, surface properties, and/or form (e.g., polymorphic form).

Medicament of any particle size may be used as a starting material for the processes, including fine particles that are suitable for use in conventional processes for preparing suspension aerosol formulations, as well as particles of a size not suitable for use in conventional processes.

The present invention also provides processes for preparing suspension formulations comprising two or more medicaments, wherein at least some of the particles for inhalation of one or more of the medicaments are formed in situ during the manufacture of the formulation.

The present invention further provides processes for preparing a suspension aerosol formulation, wherein the medicament and solvent are admixed in such proportions to partially, but not completely, dissolve the medicament. Propellant is then mixed with the medicament-solvent mixture to precipitate at least a portion of the dissolved medicament.

The present invention is applicable to the preparation of suspension aerosol formulations, including, but not limited to, the preparation of suspension aerosol formulations of medicaments which are intended to be administered, by inhalation, in the form of metered doses of aerosol spray, using a dispensing device called a metered dose inhaler (MDI).

The medicament is a pharmaceutically active agent, which is preferably useful in the therapeutic or prophylactic treatment of a disease or medical condition, or in a diagnostic technique.

BRIEF DESCRIPTION OF THE DRAWINGS

FIG. 3 is a graph showing the particle size distributions of several salmeterol xinafoate formulations prepared via dissolution of salmeterol xinafoate followed by precipitation by propellant.

FIG. 4 is a graph showing the particle size distribution of a salmeterol xinafoate formulation prepared from a mixture of solvent and salmeterol xinafoate, wherein the salmeterol xinafoate is partially dissolved in the solvent.

FIG. 5 is a graph comparing the particle size distribution of a formulation prepared according to a conventional process using micronized salmeterol xinafoate versus the particle size distribution of the formulation prepared via dissolution of salmeterol xinafoate followed by precipitation by propellant.

DETAILED DESCRIPTION OF THE INVENTION

Figure 1:
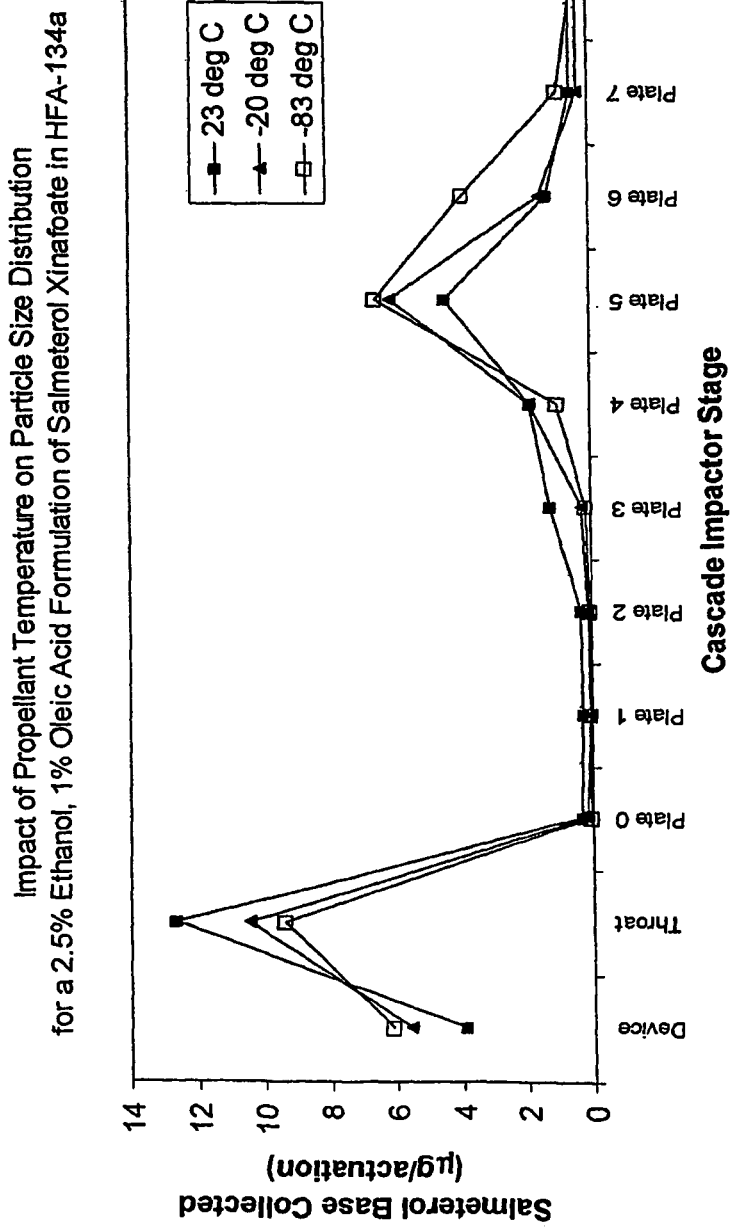
FIG. 1 is a graph showing the impact of propellant temperature on the particle size distribution obtained by Andersen cascade impaction testing of a salmeterol xinafoate formulation.

It has now been discovered, surprisingly, that the medicament particles of suspension aerosol formulations for inhalation may be generated in situ during the process of manufacturing the formulation. The medicament particles formed are of a size suitable for inhalation therapy.

Accordingly, the present invention provides, in a first aspect, a method of preparing a suspension aerosol formulation comprising a particulate medicament and a propellant, wherein a medicament solution, which includes a quantity of the medicament, is mixed with the propellant under conditions that cause a precipitate of the medicament to be formed form the solution.

The precipitate preferably comprises particles of the medicament in a form suitable for use in inhalation therapy. The precipitate can comprise particles of the medicament in a form suitable for administration to the lungs via oral or nasal inhalation, or for administration to the internal tissues of the nose via nasal inhalation. The propellant is preferably a liquefied propellant gas. The medicament can be partially precipitated when the medicament solution is mixed with the propellant.

In embodiments, the particles of the medicament in the precipitate, when aerosolized, have an MMAD of:
(a) about 0.5 to 10 µm, about 0.5 to 5 µm, or about 0.5 to 3 µm, or
(b) about 5 to 100 µm, about 5 to 50 µm, about 5 to 25 µm, about 10 to 50 µm or about 10 to 25 µm.

The medicament solution is preferably mixed with the propellant at a temperature of about −100° C. to about 40° C., about −40° C. to about 25° C., about −25° C. to about 5° C. or about −20° C. The propellant and the medicament solution can be mixed in a single step, or the propellant can be added to the medicament solution stepwise or in a plurality of aliquots.

A further excipient or further excipients can be dissolved in the medicament solution that is mixed with the propellant. A further excipient or further excipients can be in admixture with the propellant when the latter is mixed with the medicament solution. The further excipient or excipients can remain in solution, after the medicament solution has been mixed with the propellant. The further excipient or excipients can be or include a dispersing agent, preservative, flavoring, taste masking agent, buffer, antioxidant, anti-aggregating agent, co-solvent or surfactant.

An excess of propellant, beyond the minimum required to precipitate the medicament, can be mixed with the medicament solution.

In preferred embodiments, the medicament solution is mixed with the propellant in an aerosol canister. In such embodiments it is preferred for substantially all, or at least a proportion of the medicament solution to be put into the canister before the propellant. A metering valve can be fitted to the canister either before or after the propellant is added to the canister.

In further embodiments, prior to being mixed with the propellant, the medicament solution is prepared by dissolving the medicament in a solvent or solvent mixture. The medicament solution preferably comprises a solvent, or solvent mixture, that is miscible with the propellant under the mixing conditions. It is also preferred for substantially all or at least a proportion of the solvent or solvent mixture to remain present in the formulation.

In some embodiments, the medicament solution includes a plurality of medicaments. At least two of said medicaments can be dissolved in said solution, and one or more of said medicaments can remain dissolved after the solution has been mixed with the propellant. In embodiments where the solution of medicaments includes a plurality of medicaments, the precipitate can also comprises a plurality of medicaments.

In a second aspect, the present invention provides a method of preparing a suspension aerosol formulation comprising a combination of medicaments and a propellant, said method comprising separately carrying out a method in accordance with the first aspect of the invention with first and second medicaments and thereafter combining the resulting formulations to provide a single combination formulation.

In a third aspect of the invention, there is provided a process of preparing a suspension aerosol formulation, comprising the steps of:
(a) dissolving one or more medicaments in one or more solvents to form a medicament solution; and
(b) mixing one or more propellants with the solution under conditions effective to precipitate, entirely or partially, at least one of the medicaments.

The mixing of the propellant with the solution may be accomplished by adding the propellant to the solution or by adding the solution to the propellant.

The medicament may be dissolved in the solvent in a variety of ways depending on the medicament. Such methods include, but are not limited to, sonication, heating, high shearing, or stirring the medicament in the solvent.

In a yet further aspect, the invention provides a suspension aerosol formulation, comprising a particulate medicament and a propellant, prepared or preparable by a method in accordance with the invention.

In other aspects, the invention provides a method of preparing a metered dose inhaler comprising carrying out a method in accordance with the invention, and pressurized metered dose inhalers prepared or preparable by a method in accordance with the invention.

The term "suspension aerosol formulation" as used herein refers to a formulation suitable for inhalation therapy, for example an MDI formulation, wherein at least one medicament is in the form of fine particles, which are suspended or suspendable, and preferably substantially insoluble in the formulation. The term "fine particles" as used herein refers to medicament particles with an MMAD suitable for use in inhalation therapy as discussed above. Fine particles may exist, for example, in dry powder form, in suspension in a fluid, or within an aerosol.

In the conventional processes, such as disclosed in U.S. Pat. Nos. 3,014,844 and 6,743,413, fine particles in the form of dry powders are a necessary starting material for the preparation of the suspension aerosol formulations. An advantage of the processes of the present invention is that fine particles are not required as a starting material. Because the fine particles of medicament are formed from a solution of medicament, the particle size of the medicament dissolved in preparation of the solution has no impact on the size of the particles generated in the suspension aerosol formulation. Thus, the medicament employed as a starting material to prepare the formulation may be of a particle size that is suitable for the intended inhalation therapy or it may be of a particle size that is not suitable for intended inhalation therapy. For example, in preparing a suspension aerosol formulation targeting the lungs and having a desired aerosol MMAD of less than 5 µm, the medicament employed as a starting material to prepare the formulation may have a particle size (for example, a volume mean diameter, or X50, as measured by laser diffraction) less than 5 µm, or it may have a particle size greater than 5 µm. This aspect of the invention is particularly advantageous for medicaments that are known to exhibit poor flow characteristics in the micronized state. For example, as described in U.S. Pat. No. 5,795,594, conventionally micronized salmeterol xinafoate is cohesive and statically charged. As a further advantage, the use of unmicronized medicament in an aspect of the present invention averts the known safety hazards, for example inhalation hazards, associated with the handling of fine dry powders.

The suspension aerosol formulations prepared according to the present invention may be filled into or formed in aerosol canisters suitable for delivering pharmaceutical aerosol formulations. Aerosol canisters generally comprise a container or reservoir capable of withstanding the vapor pressure of the propellant used, such as a plastic bottle, a plastic-coated glass bottle, or a metal can, such as an aluminum can which may optionally be anodized, lacquer-coated and/or plastic-coated (e.g., fluoropolymer-coated).

The aerosol canister may be fitted with a metering valve capable of delivering a measured dose of the suspension aerosol formulation in the form of an aerosol. Suitable valves are commercially available from manufacturers well known in the aerosol industry, for example from Bespak (e.g. BK356), Valois (e.g. DF10), and 3M-Neotechnic Ltd. (e.g. Spraymiser). The propellant may be added to the canister through the metering valve, or the propellant may be added to the canister prior to sealing the canister with the metering valve. Prior to use, each aerosol canister is fitted into a suitable actuator for dispensing the medicament from the metering valve to the patient.

In another aspect of the invention, the suspension aerosol formulation may be formed within the aerosol canister according to a process comprising:

(a) providing an aerosol canister;

(b) charging to the aerosol canister a solution of one or more medicaments in one or more solvents;

(c) mixing one or more propellants with the solution under conditions effective to precipitate, entirely or partially, at least one of the medicaments.

Alternatively, the one or more propellants may be charged to the aerosol canister first, followed by the medicament solution.

The generation of the fine particles of the suspension formulation within the aerosol canister is a particularly advantageous aspect of the present invention, as it avoids the known problem of adhesion of fine particles onto the surfaces of the process equipment, for example the manufacturing vessel, transfer lines, and filling equipment. In the conventional processes, a suspension of fine medicament particles is prepared, and an aliquot of the suspension is subsequently transferred to each aerosol canister. Medicament may be lost from the suspension via adhesion to the process equipment as the suspension is stored and manipulated (e.g., stirred, recirculated, or transferred) prior to filling into the aerosol canister. For example, see WO 2004/045621 for additional discussion of the problem. In an aspect of the present invention, the medicament is present in a dissolved state until propellant is mixed with the medicament solution in the aerosol canister. Thus, the suspension of fine particles does not contact the process equipment, and loss of medicament particles by adhesion to the process equipment is avoided.

The present invention further provides processes for preparing a suspension aerosol formulation, wherein the medicament and solvent are admixed in such proportions to partially, but not completely, dissolve the medicament. One or more propellants are then combined with the mixture to precipitate at least a portion of the dissolved medicament.

Excipients

The term "excipient" as used herein means any chemical agent having little or no pharmacological activity (for the quantities used) but which enhances the drug formulation or the performance of the MDI system. Suspension aerosol formulations prepared by the processes of the current invention will contain, at minimum, two excipients: a solvent and a propellant.

The term "solvent" as used herein means any fluid which is used in the processes of the present invention to dissolve the medicament or a portion thereof. Suitable solvents include, for example, alcohols and polyols such as ethanol, isopropanol, n-propanol, 1-butanol, 2-butanol, 2-methyl-1-propanol, 2-methyl-2-propanol, 1-pentanol, cyclopentanol, n-hexanol, cyclohexanol, glycerol, and propylene glycol; and surfactants, for example polyethylene glycol (e.g., PEG 200 or PEG 400), oleic acid, and sorbitan trioleate. Solvents may be used singly or in combination. A particularly preferred solvent is ethanol.

The solvent is added in sufficient quantity to partially or completely dissolve the medicament. An excess of solvent, beyond the minimum required to dissolve the medicament, may be present.

The term "propellant" as used herein means one or more pharmacologically inert substance which exerts a sufficiently high vapor pressure at normal room temperature and pressure to propel a medicament from the canister of an MDI to a patient on actuation of the MDI's metering valve. Propellants are generally gases at normal room temperatures and pressures, for example at 20° C. and one atmosphere (101.325 kPa), but can be liquefied if cooled, for example to below −20 to −30° C., or compressed, for example at a pressure typically found within the canister of an MDI. Preferably, the propellant will be a weak solvent or a non-solvent for the medicament; most preferably, the propellant will be a non-solvent for the medicament. Suitable propellants include, for example, hydrofluoroalkanes such as 1,1,1,2-tetrafluoroethane ($CF_3CH_2F$)(HFA-134a) and 1,1,1,2,3,3,3-heptafluoro-n-propane ($CF_3CHFCF_3$)(HFA-227), perfluoroethane, monochloro-difluoromethane, 1,1-difluoroethane; dialkyl ethers such as dimethyl ether; and low molecular weight hydrocarbons such as n-butane, iso-butane, and propane. Propellants may be used singly or in combination. Particularly preferred propellants comprise HFA-134a and HFA-227 and mixtures thereof. Preferably, the propellant is in a substantially liquid state as it is mixed with the solution of medicament. The propellant may be used in a non-supercritical state.

In the present invention, the propellant is used as an anti-solvent to precipitate at least a portion of at least one of the one or more medicaments from solution. The propellant is preferably employed in sufficient quantity to precipitate substantially all of at least one of the medicaments from the solution of medicament. An excess of propellant, beyond the minimum required to precipitate the medicament, may be used. The propellant is preferably present in an amount sufficient to propel a plurality of therapeutically effective doses of medicament from the aerosol canister.

In the processes of the present invention, the choice of solvent and propellant, and the ratio thereof, will be dependent upon the solubility of the medicament or medicaments to be dissolved and then precipitated. A solvent-propellant combination and a solvent-propellant ratio are selected such that, under the selected process conditions, the solvent will solubilize the medicament to form a solution, and mixing the solution with propellant will precipitate at least a portion of the medicament as fine particles.

The propellant may be mixed with one or more other excipients prior to its admixture with the solution of medicament. For example, an excipient may be mixed with the propellant to modify its effectiveness as an anti-solvent. Likewise, the solvent may be mixed with one or more other excipients prior to admixture with the propellant, for example to modify the power of the solvent to dissolve the medicament. The solvent and propellant are preferably co-miscible.

Suitable excipients, in addition to propellant and solvent, which may be employed in the present invention, include but are not limited to dispersing agents, preservatives, flavorings, taste masking agents, buffers, antioxidants, antiaggregating agents, and co-solvents. The particular excipient(s) used and the concentration of the excipient(s) are selected according to the particular medicament(s) used and the desired physical properties of the formulation.

Surfactants are commonly added to suspension aerosol formulations, for example to lubricate the valve components in the inhaler device and/or improve the physical stability of the suspension. Suitable surfactants include both non-fluorinated surfactants and fluorinated surfactants known in the art and disclosed, for example in U.S. Pat. Nos. 5,849,265 and 4,352,789. Examples of suitable surfactants include oleic acid; lecithins from synthetic and natural sources, such as those available under the trade names Epikuron 200 and Phospholipon 90G; polyethylene glycol 400; sorbitan trioleate available under the trade name Span 85; sorbitan mono-oleate available under the trade name Span 80; sorbitan monolaurate available under the trade name Span 20; polyoxyethylene (20) sorbitan monolaurate available under the trade name Tween 20; oleyl polyoxyethylene (2) ether available under the trade name Brij 92; stearyl polyoxyethylene (2) available under the trade name Brij 72; oleyl polyoxyethylene (2) ether available under the trade name Genapol 0-020; lauryl polyoxyethylene (4) ether available under the trade name Brij 30; block copolymers of oxyethylene and oxypropylene available under the trade name Synperonic; poly(vinylpyridine) (PVP); diethylene glycol dioleate; tetrahydrofurfuryl oleate; ethyl oleate; isopropyl myristate; glyceryl trioleate; glyceryl mono-oleate; glyceryl monolaurate; glyceryl monostearate; glyceryl monoricinoleate; cetyl alcohol; stearyl alcohol; polyethylene glycol 400; cetyl pyridinium chloride; and oils derived from natural sources, such as, corn oil, olive oil, cotton seed oil and sunflower seed oil. Preferred surfactants are oleic acid, lecithin, and sorbitan trioleate.

Surfactants, if used, are generally present in amounts not exceeding 5 percent by weight of the total formulation, though higher amounts may be used. They will usually be present in the weight ratio 1:100 to 10:1 surfactant: medicament(s), but higher or lower surfactant: medicament(s) ratios may be employed.

The term "co-solvent" as used herein means any excipient which is added to solubilize other excipients in the suspension aerosol formulation. For example, because the surfactants typically used in MDI formulations are generally insoluble in HFA propellants, a co-solvent is commonly included in the formulation to solubilize the surfactant. Suitable co-solvents which may be used in the invention include, for example, alcohols and polyols such as ethanol, isopropanol, n-propanol, 1-butanol, 2-butanol, 2-methyl-1-propanol, 2-methyl-2-propanol, 1-pentanol, cyclopentanol, n-hexanol, cyclohexanol, glycerol, and propylene glycol. A particularly preferred co-solvent is ethanol. In the present invention, an excipient may act as both a solvent and a co-solvent.

Process Conditions

The process conditions to be used with the processes described herein may be varied to effect precipitation of the medicament or to achieve desired characteristics of the medicament particles. Generally, the process conditions which may be varied include, but are not limited to, the temperature of the propellant, the temperature of the medicament solution, and the rate at which the propellant and medicament solution are combined (e.g., the rate of addition of propellant to the medicament solution) and whether or not the propellant and/or medicament solution are maintained at an elevated pressure.

As a further example of varying the rate at which the propellant and medicament solution are combined, the propellant and medicament solution may be combined in one step or in more than one step with a delay between each step ("stepwise"; for example, adding the propellant to the medicament solution in two or more steps). Where the propellant is added to the medicament solution in a stepwise fashion, the propellant temperature may be the same at each step, or the propellant temperature may be different at each step. Likewise, where the medicament solution is added to the propellant in a stepwise fashion, the medicament solution temperature may be the same at each step, or the medicament solution temperature may be different at each step.

The optimal process conditions will depend upon the medicament and the excipients used in the process, as well as the concentrations thereof. However, these are generally selected from within ranges that ensure that the propellant is maintained in the liquid state during mixing. Thus, this step is generally carried out under pressure, or at a temperature below the propellant's boiling point.

Particle Characteristics

The processes of the invention may be controlled to achieve desired characteristics of the medicament particles generated in the suspension aerosol formulation, such as particle size and size distribution, particle shape, surface properties, and/or form (e.g., polymorphic form). Control of the particle characteristics may be accomplished by controlling such factors as the process conditions, the choice of excipients, the concentration of the excipients (for example, the ratio of solvent to propellant), the concentration of medicament in the solvent, or a combination thereof.

Without wishing to be bound by any theory, the particle size of the precipitated medicament is generally expected to decrease as the rate of the precipitation increases. The rate of medicament precipitation generally may be increased, for example, by lowering the propellant temperature, lowering the medicament solution temperature, and/or increasing the rate at which the propellant and medicament solution are combined (for example, the rate of addition of propellant to the medicament solution, or the rate of addition of medicament solution to propellant). Alternatively, the formation of larger particles may be promoted by increasing the propellant temperature, increasing the medicament solution temperature, and/or decreasing the rate at which the propellant and medicament solution are combined (for example, by combining the propellant and the medicament solution in a stepwise fashion).

Preferably, aerosol particles generated from the suspension aerosol formulations prepared according to the present invention have an MMAD suitable for delivery to a patient by inhalation. For inhalation therapy targeting the lungs, a suitable MMAD is about 0.5 to about 10 μm, more preferably about 0.5 to about 5 μm, and most preferably about 0.5 to about 3 μm. For inhalation therapy targeting the nose, where the medicament is either for the topical treatment of tissues within the nose, or to be absorbed, so as to have a systemic effect, via the nasal mucosa (i.e., via the so called intranasal route), there is a preference for aerosols in which the particles for inhalation have an MMAD of about 5 to 100 μm, preferably about 5 to 50 μm, more preferably about 5 to 25 μm, or, when penetration beyond the nasal cavity is undesirable, within the range of about 10 to 100 μm, preferably about 10 to 50 μm and more preferably about 10 to 25 μm. The MMAD of the emitted particles may be measured by conventional techniques, such as laser diffraction or by the Andersen cascade impaction or twin impinger analytical processes.

Combination Products

There is also provided, in another aspect of the present invention, processes for producing combination products. "Combination product" as used herein means a suspension aerosol formulation comprising two or more medicaments.

In one embodiment, two or more medicaments are dissolved in the same solution and then co-precipitated by the admixture of one or more propellants.

In another embodiment, each of two or more medicaments is dissolved in a separate solution in a separate container. One or more propellants are then added to each container to precipitate the medicament. The separate suspensions are then combined to form the combination product. Precipitating the medicaments in separate containers advantageously allows the particle characteristics (for example, particle size distribution) of the medicaments to be controlled independently of one another.

In another embodiment, a suspension aerosol formulation is prepared whereby one or more medicaments are precipitated to form a suspension, while one or more of the medicaments remain in solution. For example, to achieve a combination product in which one medicament is in suspension in the final formulation and another medicament is in solution in the final formulation, a solvent-propellant combination is selected such that the solvent is, effective for dissolving both medicaments, and the propellant is effective for precipitating only one of the medicaments.

Medicaments

The medicament may be one or more of any biologically active agent useful in inhalation therapy. Medicaments that may be used include, but are not limited to, beta agonists, for example albuterol, levalbuterol, salmeterol, and formoterol; glucocorticosteroids, for example beclomethasone, mometasone, budesonide, fluticasone, and triamcinolone acetonide; anti-cholinergics, for example ipratropium bromide; mast cell stabilizers, for example, cromolyn sodium; anti-allergic drugs, for example sodium cromoglycate and nedocromil sodium; and peptides and proteins, for example insulin; expectorants; antihistamines; leukotrienes synthesis inhibitors; cyclooxygenase inhibitors; or pharmacologically acceptable esters and salts and/or solvates thereof. Preferably, the medicament is present in the suspension aerosol formulation in an amount sufficient to provide a plurality of therapeutically effective doses.

Particularly preferred medicaments include salmeterol (preferably as the xinafoate salt), fenoterol (preferably as the hydrobromide salt), and ipratropium (preferably as the bromide salt).

Where applicable, the medicaments may be in the form of their racemates or in the form of their optical isomers. For example, salmeterol or a salt thereof may be used in the form of its racemate or in the form of its R(–) or S(+) enantiomer.

The concentration of medicament in the suspension aerosol formulation depends upon the desired dosage but is generally in the range of 0.005 to 5% by weight. Preferably, the medicament is present in the suspension aerosol formulation in an amount sufficient to provide a plurality of therapeutically effective doses.

DETAILED DESCRIPTION OF PREFERRED EMBODIMENTS

While the present invention may be embodied in many different forms, disclosed herein are specific embodiments thereof that exemplify the principles of the invention. It should be emphasized that the present invention is not limited to the specific embodiments illustrated.

In a first embodiment, the present invention may be employed for the preparation of suspension aerosol formulations comprising salmeterol xinafoate. Salmeterol xinafoate and ethanol are combined to form a solution. The concentration of salmeterol xinafoate contained in the ethanol is preferably sufficient to provide a plurality of therapeutically effective doses from the suspension aerosol formulation. Depending on the amount of salmeterol xinafoate to be dissolved, it may be necessary to warm the mixture of salmeterol xinafoate and ethanol to achieve dissolution. Salmeterol xinafoate is generally employed at concentrations which are amenable to dissolution of the salmeterol xinafoate in the ethanol at about room temperature (25° C.) or less, though higher salmeterol xinafoate concentrations may be employed, requiring higher dissolution temperatures.

The propellant may be added to the salmeterol xinafoate solution, or the salmeterol xinafoate solution may be added to the propellant. Accordingly, an aliquot of the salmeterol xinafoate solution is dispensed into an aerosol canister and a metering valve is crimp sealed to the canister. Propellant is added through the valve, whereby the salmeterol xinafoate is precipitated as fine particles suitable for inhalation therapy.

On its addition to the salmeterol xinafoate solution, the propellant is desirably at a temperature of about −100° C. to about 40° C., preferably about −40° C. to about 25° C., more preferably about −25° C. to about 5° C., and most preferably about −20° C. The propellant may be added in more than one step, though preferably the propellant is added in one step.

Preferred propellants are HFA-134a, HFA-227, and mixtures thereof. HFA-134a is especially preferred.

In an alternate process of the first embodiment, the salmeterol xinafoate and ethanol solution is formed in a process vessel, and the propellant is added to the process vessel to form the suspension aerosol formulation. An aliquot of the suspension aerosol formulation is then transferred to an aerosol canister, either before or after the canister is fitted with a metering valve.

In a second embodiment, the present invention may be employed for the preparation of suspension aerosol formulations comprising fenoterol hydrobromide. Fenoterol hydrobromide and ethanol are combined to form a solution. The concentration of fenoterol hydrobromide contained in the ethanol is preferably sufficient to provide a plurality of therapeutically effective doses from the suspension aerosol formulation. Depending on the amount of fenoterol hydrobromide to be dissolved, it may be necessary to warm the mixture of fenoterol hydrobromide and ethanol to achieve dissolution. Fenoterol hydrobromide is generally employed at concentrations which are amenable to dissolution of the fenoterol hydrobromide in the ethanol at about 60° C. or less, though higher fenoterol hydrobromide concentrations may be employed, requiring higher dissolution temperatures.

The propellant may be added to the fenoterol hydrobromide solution, or the fenoterol hydrobromide solution may be added to the propellant. Accordingly, an aliquot of the fenoterol hydrobromide solution is dispensed into an aerosol canister and propellant is added, whereby the fenoterol hydrobromide is precipitated as fine particles suitable for inhalation therapy. A metering valve is crimp sealed to the canister.

On its addition to the fenoterol hydrobromide solution, the propellant is desirably at a temperature of about −100° C. to about 40° C., preferably about −100° C. to about 25° C., more preferably about −0° C. to about 5° C., and most preferably about −45° C. The propellant may be added in more than one step, though preferably the propellant is added in one step.

Preferred propellants are HFA-134a, HFA-227, and mixtures thereof. HFA-227 is especially preferred.

In a third embodiment, the present invention may be employed for the preparation of suspension aerosol formulations comprising ipratropium bromide. Ipratropium bromide and ethanol are combined to form a solution. The concentration of ipratropium bromide contained in the ethanol is preferably sufficient to provide a plurality of therapeutically effective doses from the suspension aerosol formulation. Depending on the amount of ipratropium bromide to be dissolved, it may be necessary to warm the mixture of salmeterol xinafoate and ethanol to achieve dissolution. Ipratropium bromide is generally employed at concentrations which are amenable to dissolution of the ipratropium bromide in the ethanol at about 50° C. or less, though higher ipratropium bromide concentrations may be employed, requiring higher dissolution temperatures.

The propellant may be added to the ipratropium bromide solution, or the ipratropium bromide solution may be added to the propellant. Accordingly, an aliquot of the ipratropium bromide solution is dispensed into an aerosol canister and propellant is added, whereby the ipratropium bromide is precipitated as fine particles suitable for inhalation therapy. A metering valve is crimp sealed to the canister.

On its addition to the ipratropium bromide solution, the propellant is desirably at a temperature of about −100° C. to about 40° C., preferably about −100° C. to about 25° C., more preferably about −80° C. to about 5° C., and most preferably about 45° C. The propellant may be added in more than one step, though preferably the propellant is added in one step.

Preferred propellants are HFA-134a, HFA-227, and mixtures thereof. HFA-227 is especially preferred.

EXAMPLES

The following Examples are provided to illustrate the present invention and should not be construed as limiting thereof. The formulations herein are described in terms of the concentration of ethanol (EtOH) (percent w/w based on the weight of propellant) and the concentration of oleic acid or lecithin (percent w/w based on the weight of medicament). The formulations were filled into uncoated aluminum aerosol canisters or aluminum aerosol canisters having a fluoropolymer coating comprising either an ethylenetetrafluoroethylene copolymer (ETFE) or a blend of perfluorinated ethylene propylene copolymer (FEP) and polyethersulphone (PES). Aerosol canisters were fitted with metering valves obtained from Bespak. As observed visually in glass bottles, formulations prepared according to the present invention were in the form of suspensions which were readily dispersed by hand shaking. The suspension stability is suitable for use with a metered dose inhaler.

Particle size distributions of the aerosol particles generated from the suspension aerosol formulations were determined using an 8-stage Andersen cascade impactor (ACI) with USP induction port, available from Thermo-Andersen (Smyrna, Ga.). MMAD and GSD were calculated from the ACI data as prescribed by the *European Pharmacopoeia* 5 (2004). ACI testing was performed using Bespak or Nemo actuators having orifice diameters of about 0.33 mm. The salmeterol formulations are intended to deliver about 25 µg of salmeterol per actuation from the valve. The fenoterol and ipratropium formulations are intended to deliver about 50 µg of drug substance per actuation from the valve.

Example 1

Control of Particle Size and Size Distribution

A mixture of 0.27 g of salmeterol xinafoate, 20.0 g of 200 proof ethanol USP, and 0.0027 g of oleic acid NF was contained in a flask and stirred and sonicated until a clear solution was obtained. A 0.50-g aliquot of the solution was added to each of three 19-mL fluoropolymer (FEP-PES) coated aluminum canisters. A 100-µL metering valve was crimp sealed to each canister, and 20 g of HFA-134a, at 20° C., was added to each canister, in one step, through the valve using a Pamasol filler.

Example 2

Control of Particle Size and Size Distribution

A mixture of 0.51 g of salmeterol xinafoate, 37.6 g of 200 proof ethanol USP, and 0.0051 g of oleic acid NF was stirred and sonicated until a clear solution was obtained. A 0.48-g aliquot of the solution was added to each of three 19-mL fluoropolymer (FEP-PES) coated aluminum canisters. A 100-µL metering valve was crimp sealed to each canister, and 19 g of HFA-134a, at −20° C., was added to each canister, in one step, through the valve using a Pamasol filler.

Example 3

Control of Particle Size and Size Distribution

A mixture of 0.26 g of salmeterol xinafoate, 18.7 g of 200 proof ethanol USP, and 0.0024 g of oleic acid NF was stirred and sonicated until a clear solution was obtained. A 0.47-g aliquot of the solution was added to each of three 19-mL fluoropolymer (FEP-PES) coated aluminum canisters. An 18-g aliquot of HFA-134a, at −83° C., was added to each canister in one step. A 100-µL metering valve was then crimp sealed to each canister.

The following table provides a comparison of Andersen cascade impaction data obtained for formulations from Examples 1-3. A graph of the particle size distribution from each of Examples 1-3 is provided as FIG. 1. The results illustrate that by controlling the temperature of the propellant, medicament particles having different size distributions can be produced. The observed MMAD decreased with decreasing propellant temperature.

| Impact of Propellant Temperature | | | |
|---|---|---|---|
| | Example 1 | Example 2 | Example 3 |
| | | Formulation | |
| | 2.5% EtOH; 1% oleic acid; HFA-134a | 2.5% EtOH; 1% oleic acid; HFA-134a | 2.5% EtOH; 1% oleic acid; HFA-134a |
| | | Propellant Temperature | |
| | 20° C. | −20° C. | −83° C. |
| MMAD (μm) | 1.8 | 1.6 | 1.2 |
| GSD | 2.0 | 1.5 | 1.5 |
| Replications | 3 | 3 | 3 |

Example 4

Control of Particle Size and Size Distribution

A mixture of 0.51 g of salmeterol xinafoate, 37.6 g of 200 proof ethanol USP, and 0.0051 g of oleic acid NF was stirred and sonicated until a clear solution was obtained. A 0.48-g aliquot of the solution was added to each of three 19-mL fluoropolymer (FEP-PES) coated aluminum canisters. A 100-μL metering valve was crimp sealed to each canister, and 9 g of HFA-134a, at −20° C., was added to each canister through the valve using a Pamasol filler. After 10 min, 10 g of HFA-134a, at −20° C., was added to each canister through the valve using a Pamasol filler. Thus, Example 4 illustrates the addition of propellant in two steps.

Figure 2:
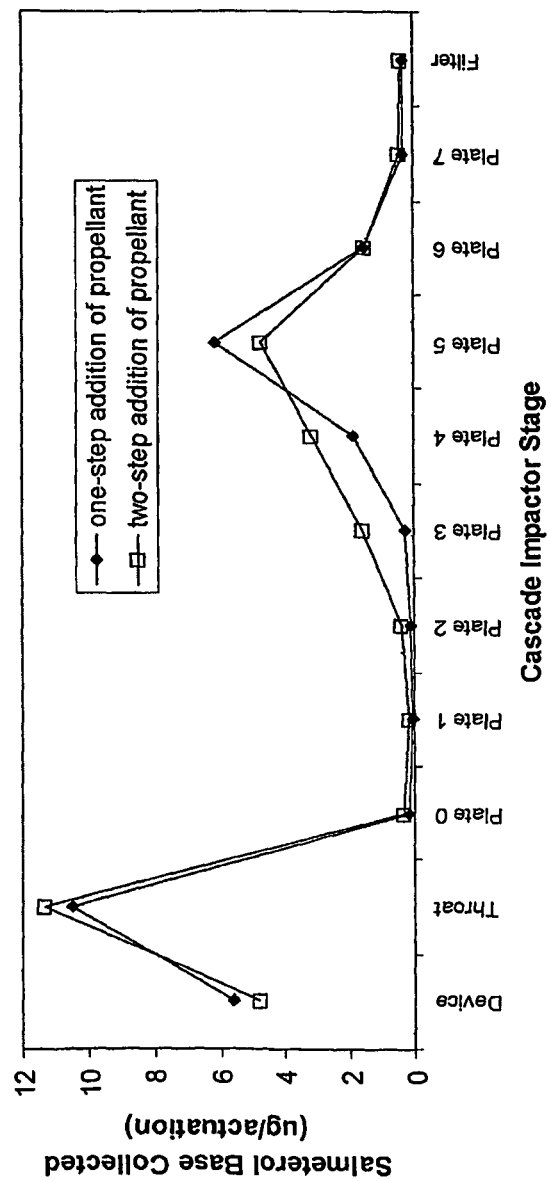
FIG. 2 is a graph comparing the particle size distribution of a salmeterol xinafoate formulation prepared by the addition of propellant in one step versus the particle size distribution of the same formulation prepared by the addition of propellant in two steps.
Figure 6:
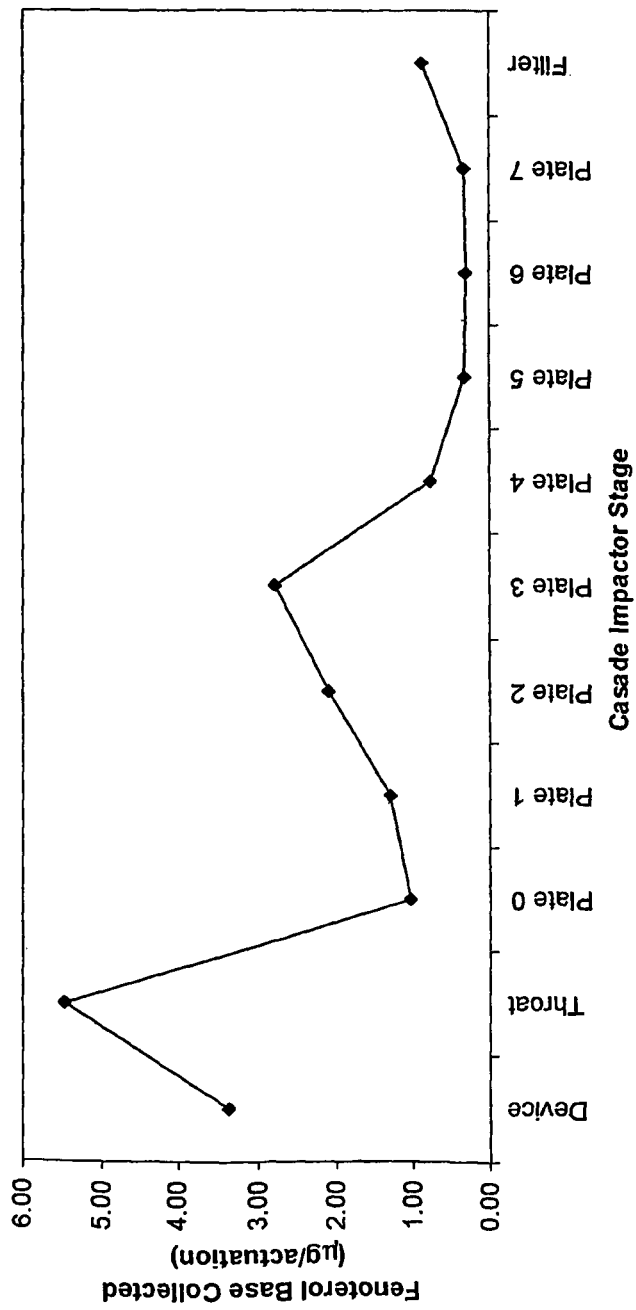
FIG. 6 is a graph of the particle size distribution of a fenoterol hydrobromide formulation prepared via dissolution of fenoterol hydrobromide followed by precipitation by propellant.
Figure 7:
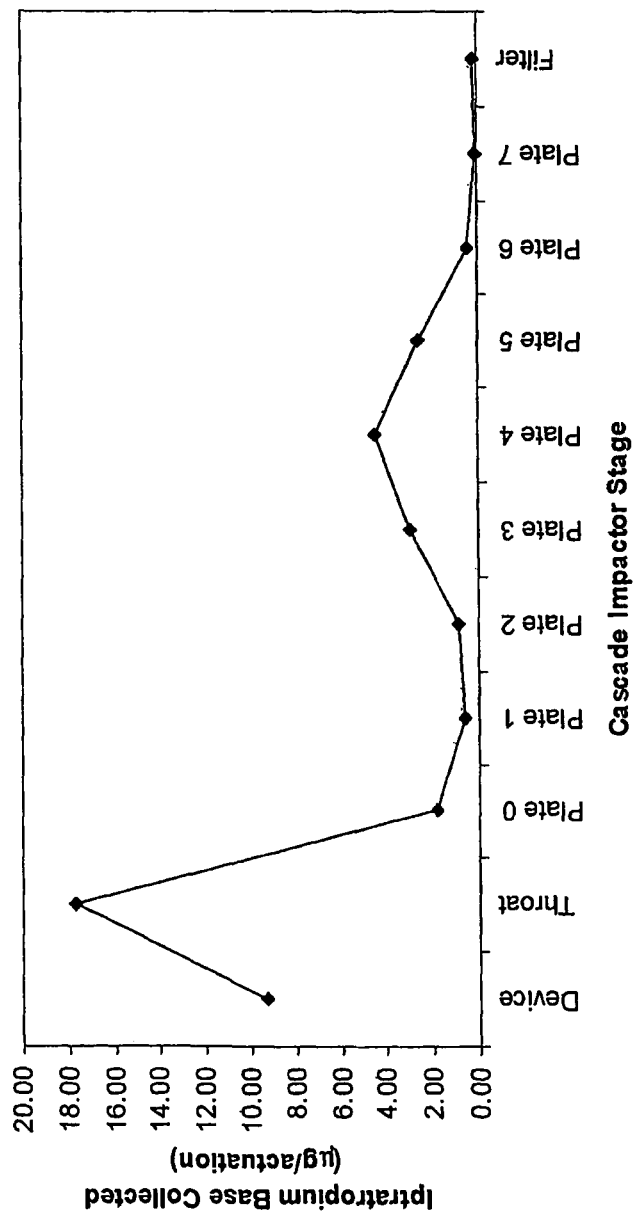
FIG. 7 is a graph of the particle size distribution of a ipratropium bromide formulation prepared via dissolution of ipratropium bromide followed by precipitation by propellant.

The following table provides a comparison of Andersen cascade impaction results for formulations from Examples 2 and 4. A graph of the particle size distributions is provided as FIG. 2. The results illustrate that by controlling whether the propellant is added in one or two steps, medicament particles having different size distributions can be produced.

| Impact of One-step vs. Two-Step Addition of Propellant | | |
|---|---|---|
| | Example 2 | Example 4 |
| | Formulation | |
| | 2.5% EtOH; 1% oleic acid; HFA-134a | 2.5% EtOH; 1% oleic acid; HFA-134a |
| | One- or Two-Step Addition of Propellant | |
| | One step | Two steps |
| | Propellant Addition Temperature | |
| | −20° C. | −20° C. |
| MMAD (μm) | 1.6 | 1.9 |
| GSD | 1.5 | 1.9 |
| Replications | 3 | 3 |

Example 5

Preparation of a Salmeterol Xinafoate Formulation with 3% Ethanol and 2% Lecithin in HFA-227

A stock solution of 171.2 g of ethanol USP and 0.0352 g of lecithin (Phospholipon 90G) was prepared. A 17.1 g aliquot of the stock solution was mixed with 0.17 g of salmeterol xinafoate, with stirring and sonication until a clear solution of medicament was obtained. A 0.6-g aliquot of the clear medicament solution was added to each of three 19-mL fluoropolymer (FEP-PES) coated aluminum canisters. A 100-μL metering valve was crimp sealed to each canister, and 19 g of HFA-227, at −20° C., was added to each canister, in one step, through the valve using a Pamasol filler.

Example 6

Preparation of a Salmeterol Xinafoate Formulation with 3% Ethanol and 2% Lecithin in HFA-134a A stock solution of 147.9 g of ethanol USP and 0.0415 g of lecithin (Phospholipon 90G) was prepared. A 14.8 g aliquot of the stock solution was mixed with 0.17 g of salmeterol xinafoate, with stirring and sonication until a clear solution of medicament was obtained. A 0.5 g aliquot of the clear medicament solution was added to each of three 19-mL fluoropolymer (FEP-PES) coated aluminum canisters. A 100-μL metering valve was crimp sealed to each canister, and 17 g of HFA-134a, at −20° C., was added to each canister, in one step, through the valve using a Pamasol filler.

Example 7

Preparation of a Salmeterol Xinafoate Formulation with 2% Ethanol and 2% Oleic Add in HFA-227

A stock solution of 115.3 g of ethanol USP and 0.0353 g of oleic acid was prepared. An 11.6-g aliquot of the stock solution was mixed with 0.17 g of salmeterol xinafoate, with stirring and sonication until a clear solution of medicament was obtained. A 0.4-g aliquot of the clear medicament solution was added to each of three 19-mL fluoropolymer (FEP-PES) coated aluminum canisters. A 100-μL metering valve was crimp sealed to each canister, and approximately 19.5 g of HFA-227, at −20° C., was added to each canister through the valve, in one step, using a Pamasol filer.

The following table provides a comparison of Andersen cascade impaction results for formulations from Examples 2 and 5-7. A graph of the particle size distributions is provided as FIG. 3. The results illustrate the use of the processes of the invention to prepare a variety of salmeterol xinafoate formulations.

| Salmeterol Xinafoate Formulations | | | | |
|---|---|---|---|---|
| | Example 2 | Example 5 | Example 6 | Example 7 |
| | | Formulation | | |
| | 2.5% EtOH; 1% oleic acid; HFA-134a | 3% EtOH; 2% lecithin; HFA-227 | 3% EtOH; 2% lecithin; HFA-134a | 2% EtOH; 2% oleic acid; HFA-227 |
| MMAD (μm) | 1.6 | 2.0 | 1.8 | 1.7 |
| GSD | 1.5 | 1.8 | 1.7 | 1.5 |
| Replications | 3 | 3 | 3 | 3 |

Example 8

Partial Dissolution of Medicament

A mixture of 0.27 g of salmeterol xinafoate, 5.1 g of 200 proof ethanol USP, and 0.0027 g of oleic acid NF was stirred and sonicated to achieve a suspension of medicament. A 0.13- to 0.14-g aliquot of the suspension was added to each of three 15-mL fluoropolymer (FEP-PES) coated aluminum canisters. A 63-μL metering valve was crimp sealed to each canister, and 13 g of HFA-134a, at 4° C., was added to each canister, in one step, through the valve using a Pamasol filler.

The following table summarizes the Andersen cascade impaction results for the formulation of Example 8. A graph of the particle size distribution is provided as FIG. 4. The results illustrate the use of partially dissolved medicament in a process of the current invention. The use of partially dissolved medicament resulted in a larger MMAD compared to similar formulations prepared from a solution of completely dissolved medicament.

| Impact of Partial Dissolution of Medicament | |
|---|---|
| Formulation | Example 8<br>1% EtOH; 1% oleic acid; HFA-134a |
| MMAD (μm) | 3.2 |
| GSD | 2.7 |
| Replications | 3 |

Example 9

Preparation of a Salmeterol Xinafoate Formulation with 2% Ethanol and 1% Oleic Acid in HFA-134a A stock solution of 22.3 g of ethanol USP and 0.00577 g of oleic acid was prepared. A 2.23 g aliquot of the stock solution was mixed with 0.0577 g of salmeterol xinafoate, with stirring and sonication until a clear solution of medicament was obtained. A 0.23 g aliquot of the clear medicament solution was added to each of three 19-mL fluoropolymer (ETFE) coated aluminum canisters. Approximately 11.2 g of HFA-134a, at −45° C., was added to each canister in one step. A 63-μL metering valve was crimp sealed to each canister.

Example 10 (Comparative Example)

Preparation of a Salmeterol Xinafoate Formulation Using a Conventional Process The following illustrates the preparation of a salmeterol xinafoate formulation using a conventional process, in that conventionally micronized medicament was employed with care to avoid dissolution of the medicament. Dissolution of the medicament was prevented by mixing the medicament with propellant prior to the addition of ethanol and oleic acid.

A stock solution of 16.0 g of ethanol USP and 0.0053 g of oleic acid was prepared. Into each of three 14-mL fluoropolymer (FEP-PES) coated aluminum canisters was added 7 mg of micronized salmeterol xinafoate, having a volume mean diameter (X50) of 1.6 μm as measured using a Sympatec laser diffraction instrument. To each canister was then added 10.0 g of HFA-134a, at about −70° C., and approximately 0.20 g of the stock solution. A 50-μL metering valve was crimp sealed to each canister. Each canister was sonicated for 1.5 minutes to promote mixing of the formulation and deaggregation of the medicament particles.

The results for Example 9 and the conventional process (Comparative Example) are given in the table below. A graph of the particle size distributions is provided as FIG. 5. Compared to the conventional process, the process of the current invention provided aerosol particles with a smaller MMAD.

| Comparison to a Conventional Process | | |
|---|---|---|
| | Process | |
| | Example 9 | Conventional Process<br>(Comparative Example) |
| | Formulation | |
| | 2% EtOH, 1% oleic acid;<br>HFA-134a | 2% EtOH, 1% oleic acid;<br>HFA-134a |
| MMAD (μm) | 1.8 | 2.6 |
| GSD | 2.6 | 1.5 |
| Replications | 3 | 3 |

Example 11

Preparation of a Fenoterol Hydrobromide Formulation with 0.63% Ethanol and 1% Oleic Acid in HFA-227

A mixture of 107 mg of fenoterol hydrobromide, 10.8 mg of oleic acid, and 1.5 g of ethanol USP was prepared. This mixture was stirred, heated to approximately 60° C., and sonicated until a clear solution of medicament was obtained. A 162-mg aliquot of the solution was added to each of three 22-mL uncoated aluminum canisters. Approximately 24 g of HFA-227 propellant, chilled to −45° C., was then added to each canister. A 100-μL metering valve was then crimped to each canister.

| Fenoterol Hydrobromide Formulation | |
|---|---|
| Formulation | Example 11<br>0.63% EtOH; 1% oleic acid; HFA-227 |
| MMAD (μm) | 4.1 |
| GSD | 1.8 |
| Replications | 3 |

Example 12

Preparation of an Ipratropium Bromide Formulation with 0.62% Ethanol and 1% Oleic Acid in A mixture of 52.8 mg of ipratropium bromide, 5.3 mg of oleic acid, and 0.7416 g of ethanol USP was prepared. The mixture was stirred, heated to 50° C., and sonicated until a clear solution of medicament was obtained. A 159-mg aliquot of the solution was added to each of three 22-mL uncoated aluminum cans. Approximately 24 g of HFA-227, chilled to −45° C., was then added to each canister. A 100-μL metering valve was then crimped to each canister.

| Ipratropium Bromide Formulation | |
|---|---|
| Formulation | Example 12<br>0.62% EtOH; 1% oleic acid; HFA-227 |
| MMAD (μm) | 3.2 |
| GSD | 1.8 |
| Replications | 1 |

The invention claimed is:

1. A method of preparing a suspension aerosol formulation comprising a particulate medicament and a propellant, wherein a medicament solution is mixed with the propellant under conditions that cause a precipitate of the medicament to be formed from the solution, wherein the medicament solution is mixed with the propellant in an aerosol canister, and wherein the precipitate comprises particles of the medicament in a form suitable for use in inhalation therapy.

2. A method as claimed in claim 1, wherein the precipitate comprises particles of the medicament in a form suitable for administration to the lungs via oral or nasal inhalation, or for administration to the internal tissues of the nose via nasal inhalation.

3. A method as claimed in claim 1, wherein the propellant is a liquefied propellant gas.

4. A method as claimed in claim 1, wherein the medicament is partially precipitated when the medicament solution is mixed with the propellant.

5. A method as claimed in claim 1, wherein the particles of the medicament in the precipitate, when aerosolized, have an MMAD selected from the group consisting of about 0.5 to 10 μm, about 0.5 to 5 μm, about 0.5 to 3 μm, about 5 to 100 μm, about 5 to 50 μm, about 5 to 25 μm, about 10 to 50 μm, and about 10 to 25 μm.

6. A method as claimed in claim 1, wherein the medicament solution is mixed with the propellant at a temperature of about −100° C. to about 40° C.

7. A method as claimed in claim 1, wherein the propellant and the medicament solution are mixed in a single step, or the propellant is added to the medicament solution stepwise or in a plurality of aliquots.

8. A method as claimed in claim 1, wherein a further excipient or further excipients is or are dissolved in the medicament solution that is mixed with the propellant.

9. A method as claimed in claim 8, wherein the further excipient or excipients remain in solution, after the medicament solution has been mixed with the propellant.

10. A method as claimed in claim 1, wherein a further excipient or further excipients is or are in admixture with the propellant when the latter is mixed with the medicament solution.

11. A method as claimed in claim 10, wherein the further excipient or excipients remain in solution, after the medicament solution has been mixed with the propellant.

12. A method as claimed in claim 1, wherein an excess of propellant, beyond the minimum required to precipitate the medicament, is mixed with the medicament solution.

13. A method as claimed in claim 1, wherein substantially all, or at least a proportion of the medicament solution is put into the canister before the propellant.

14. A method as claimed in claim 13, wherein a metering valve is fitted to said canister either before or after the propellant is added to the canister.

15. A method as claimed in claim 1, wherein, prior to being mixed with the propellant, the medicament solution is prepared by dissolving the medicament in a solvent or solvent mixture.

16. A method as claimed in claim 15, wherein the solvent is, or the solvent mixture includes an alcohol, polyol or surfactant.

17. A method as claimed in claim 1, wherein the medicament solution comprises a solvent, or solvent mixture, that is miscible with the propellant under the mixing conditions.

18. A method as claimed in claim 17, wherein all or at least a portion of the solvent or solvent mixture remains present in the formulation.

19. A method as claimed in claim 17, wherein the solvent is, or the solvent mixture includes an alcohol, polyol or surfactant.

20. A method as claimed in claim 1, wherein the propellant is a weak or non-solvent for the medicament.

21. A method as claimed in claim 1, wherein two or more propellants are mixed with the medicament solution.

22. A method as claimed in claim 1, wherein the propellant is or the propellants include a hydrofluoroalkane, dialkyl ether, or low molecular weight hydrocarbon.

23. A method as claimed in claim 22, wherein the propellant is or the propellants include 1,1,1,2-tetrafluoroethane (HFA-134a), or 1,1,1,2,3,3,3-heptafluoro-n-propane (HFA-227) or a mixture thereof.

24. A method as claimed in claim 1, wherein, the medicament is a beta agonist, glucocorticosteroid, anti-cholinergic, mast cell stabilizer, anti-allergic drug, peptide, protein, expectorant, antihistamine, leukotriene synthesis inhibitor, or cyclooxygenase inhibitor.

25. A method as claimed in claim 24, wherein the medicament is salmeterol, optionally as the xinafoate salt, fenoterol, optionally as the hydrobromide salt or ipratropium, optionally as the bromide salt.

26. A method as claimed in claim 1, wherein the medicament solution includes a plurality of medicaments.

27. A method as claimed in claim 26, wherein there are two medicaments dissolved in said solution.

28. A method as claimed in claim 27, wherein one or more of said dissolved medicaments remains in solution after the medicament solution is mixed with the propellant.

29. A method as claimed in claim 26, wherein the precipitate comprises a plurality of medicaments.

30. A method as claimed in claim 1, wherein the concentration of medicament in the formulation is about 0.0005 to 5% by weight.

31. A method as claimed in claim 1, comprising the steps of:
(a) dissolving one or more medicaments in one or more solvents to form a solution; and
(b) mixing one or more propellants with said solution under conditions effective to precipitate, entirely or partially, at least one of said one or more medicaments.

32. The method of claim 31, wherein said solution is contained in an aerosol canister, further comprising the step of fitting a metering valve to said aerosol canister, wherein said one or more propellants is added through the metering valve to said solution.

33. The method of claim 31, wherein said solution is contained in an aerosol canister, further comprising the step of fitting a metering valve to said aerosol canister after said one or more propellants is added to said solution.

34. The method of claim 31, wherein the mixing step comprises adding the one or more propellants to the solution.

35. The method of claim 31, wherein said one or more solvents is ethanol.

36. The method of claim 31, wherein said one or more propellants is selected from the group consisting of HFA-134a and HFA-227.

37. The method of claim 31, wherein said one or more medicaments is salmeterol xinafoate.

38. The method of claim 37, wherein said one or more solvents is ethanol.

39. The method of claim 37, wherein said one or more propellants is HFA-134a.

40. The method of claim 37, wherein said one or more propellants are at a temperature of about −100° C. to about 40° C.

41. The method of claim 37, wherein said one or more propellants are at a temperature of about −40° C. to about 25° C.

42. The method of claim 37, wherein said one or more propellants are at a temperature of about −25° C. to about 5° C.

43. The method of claim 37, wherein said one or more propellants are at a temperature of about −20° C.

44. The method of claim 37, wherein said one or more propellants are in a non-supercritical state.

45. The method of claim 31, wherein one of said one or more medicaments is fluticasone propionate, mometasone, albuterol or a salt or solvate thereof.

46. The method of claim 31, wherein said one or more medicaments is salmeterol xinafoate and fluticasone propionate.

47. The method of claim 31, wherein said suspension aerosol formulation produces a particle MMAD less than about 100 μm when said suspension aerosol formulation is aerosolized.

48. The method of claim 31, wherein said suspension aerosol formulation produces a particle MMAD of between about 0.5 μm and about 10 μm when said suspension aerosol formulation is aerosolized.

49. The method of claim 31, wherein said suspension aerosol formulation produces a particle MMAD of between about 0.5 μm and about 5 μm when said suspension aerosol formulation is aerosolized.

50. A method of producing a pressurized metered dose inhaler, comprising carrying out a method as claimed in claim 1.

51. A pressurized metered dose inhaler produced by a method as claimed in claim 50.

52. A suspension aerosol formulation, comprising a particulate medicament and a propellant, prepared by a method as claimed in claim 1.

53. A method as claimed in claim 8, wherein the further excipient or excipients is or include a dispersing agent, preservative, flavoring, taste masking agent, buffer, antioxidant, anti-aggregating agent, co-solvent or surfactant.

54. A method as claimed in claim 10, wherein the further excipient or excipients is or include a dispersing agent, preservative, flavoring, taste masking agent, buffer, antioxidant, anti-aggregating agent, co-solvent or surfactant.

55. A method as claimed in claim 16, wherein the solvent is, or the solvent mixture includes ethanol.

56. A method as claimed in claim 19, wherein the solvent is, or the solvent mixture includes ethanol.

57. A method as claimed in claim 1, wherein said medicament is one or more selected from the group consisting of beta agonists, glucocorticosteroids, anti-cholinergics, mast cell stabilizers, anti-allergic drugs, peptides, proteins, expectorants, antihistamines, leukotriene synthesis inhibitors, cyclooxygenase inhibitors, and pharmaceutically acceptable salts and solvates thereof.

58. A method as claimed in claim 1, wherein said medicament is one or more selected from the group consisting of albuterol, levalbuterol, salmeterol, formoterol, beclomethasone, mometasone, budesonide, fluticasone, triamcinolone acetonide, ipratropium bromide, cromolyn sodium, sodium cromoglycate nedocromil sodium, insulin, and pharmaceutically acceptable salts and solvates thereof.

59. A method as claimed in claim 6, wherein the medicament solution is mixed with the propellant at a temperature selected from the group consisting of about −40° C. to about 25° C., about −25° C. to about 5° C., and about −20° C.

* * * * *